(12) United States Patent
Young et al.

(10) Patent No.: US 9,445,264 B2
(45) Date of Patent: Sep. 13, 2016

(54) SYSTEM AND METHOD FOR ESTABLISHING A SECURED CONNECTION BETWEEN AN IMPLANTABLE MEDICAL DEVICE AND AN EXTERNAL DEVICE

(71) Applicant: Pacesetter, Inc., Sunnyvale, CA (US)

(72) Inventors: Chao-Wen Young, Cupertino, CA (US); Yongjian Wu, Saratoga, CA (US); Min Yang, Los Altos, CA (US); Erik Shreve, Dallas, TX (US); Andrew Rissing, McKinney, TX (US); Jun Yang, Valencia, CA (US); Thanh Tieu, Simi Valley, CA (US); Mostafa Sadeghi, Los Angeles, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 120 days.

(21) Appl. No.: 14/285,243

(22) Filed: May 22, 2014

(65) Prior Publication Data

US 2015/0341785 A1 Nov. 26, 2015

(51) Int. Cl.
*A61N 1/372* (2006.01)
*H04W 12/04* (2009.01)
*A61N 1/36* (2006.01)
*A61N 1/05* (2006.01)

(52) U.S. Cl.
CPC ............ *H04W 12/04* (2013.01); *A61N 1/0551* (2013.01); *A61N 1/3605* (2013.01); *A61N 1/37217* (2013.01); *A61N 1/37252* (2013.01); *H04L 2209/88* (2013.01)

(58) Field of Classification Search
CPC ..................... A61N 1/37276; A61N 1/37252

USPC ........................................................ 607/60
See application file for complete search history.

(56) References Cited

U.S. PATENT DOCUMENTS

| | | | |
|---|---|---|---|
| 6,230,272 B1 * | 5/2001 | Lockhart ................. | G06F 21/62 726/2 |
| 7,212,110 B1 | 5/2007 | Martin et al. | |
| 7,228,179 B2 | 6/2007 | Campen et al. | |
| 7,571,007 B2 | 8/2009 | Erickson et al. | |
| 9,054,436 B2 | 6/2015 | Swanson et al. | |
| 2006/0135064 A1 | 6/2006 | Cho et al. | |

(Continued)

FOREIGN PATENT DOCUMENTS

WO 01/93953 A1 12/2001

OTHER PUBLICATIONS

Bluetooth Specification, Version 4.1, vol. 3, Dec. 3, 2014, pp. 608-638, Bluetooth SIG, Inc., accessed at https://www.bluetooth.org/en-us/specification/adopted-specifications.

*Primary Examiner* — Alyssa M Alter
(74) *Attorney, Agent, or Firm* — Theresa A. Raymer

(57) ABSTRACT

A system and method are provided for initiating a secured bi-directional communication session with an implantable medical device. The system and method include configuring a pulse generator (PG) device and an external device to establish a communication link there between through a wireless protocol with a defined bonding procedure. The system and method also include transmitting a static identification and dynamic seed from the PG device through a dedicated advertisement channel to the external device and generating a passkey from a pre-defined algorithm based on the dynamic seed and a static identification. Further, the system and method include starting the defined bonding procedure.

18 Claims, 7 Drawing Sheets

(56) References Cited

U.S. PATENT DOCUMENTS

| | | |
|---|---|---|
| 2006/0170486 A1 | 8/2006 | Tranchina et al. |
| 2007/0229269 A1* | 10/2007 | Morris ................ G06K 7/0008 340/572.1 |
| 2009/0326608 A1 | 12/2009 | Huynh et al. |
| 2014/0343564 A1 | 11/2014 | Feler et al. |
| 2015/0148868 A1* | 5/2015 | Shahandeh ........ A61N 1/37276 607/60 |

\* cited by examiner

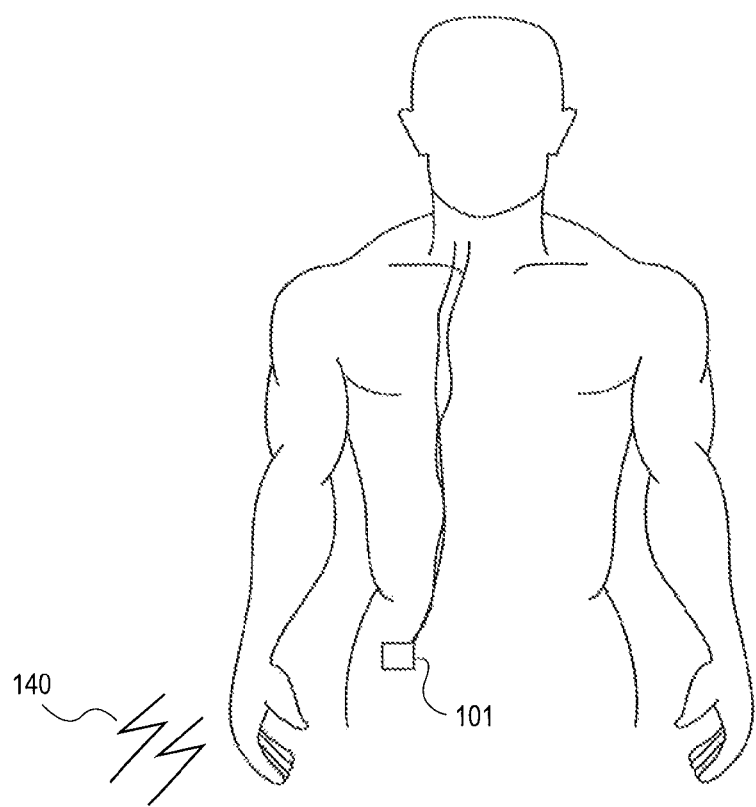
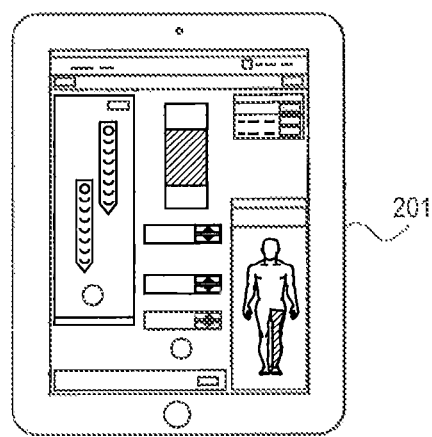
FIG. 1

SYSTEM AND METHOD FOR ESTABLISHING A SECURED CONNECTION BETWEEN AN IMPLANTABLE MEDICAL DEVICE AND AN EXTERNAL DEVICE

BACKGROUND OF THE INVENTION

Embodiments of the present disclosure generally relate to systems and methods for establishing a secured bi-directional communication session between devices, and more particularly to establishing a communication session between implantable medical devices and external devices.

An implantable medical device ("IMD") is a medical device that is configured to be implanted within a patient anatomy and commonly employ one or more leads with electrodes that either receive or deliver voltage, current or other electromagnetic pulses (generally "energy") from or to an organ or tissue for diagnostic or therapeutic purposes. In general, IMDs include a battery, electronic circuitry, such as a pulse generator and/or a microprocessor that is configured to handle RF communication with an external device as well as control patient therapy. The components of the IMD are hermetically sealed within a metal housing (generally referred to as the "can").

IMDs are programmed by and transmit data to external devices controlled by physicians and/or the patient. The external devices communicate by forming wireless bi-directional communication links with the IMDs. Restrictions may be placed on which external device may form a wireless bi-directional communication link with the IMD. For example, an external device of the patient (e.g., patient's programmer) may only be configured to form a wireless bi-directional communication link with the IMD implanted in the patient. However, the external device of the clinician (e.g., doctor, nurse) may be configured to form wireless bi-directional communication links with multiple IMDs.

Recently, these external devices may communicate using Bluetooth, WiFi, or other commercial protocols compatible with commercial wireless devices such as tablet computers, smartphones, and the like. However, commercial protocols have limited pairing procedures for establishing secure communication links. Further, commercial protocols may require a user interface for each device to, for example, provide security keys or passkeys to establish the secured connection. A need exists for improved methods and systems that establish a secure communication link with an IMD using a commercial protocol.

BRIEF SUMMARY

In accordance with an embodiment herein, a method is provided for initiating a secured bi-directional communication session with an implantable medical device. The method includes configuring a pulse generator (PG) device and an external device to establish a communication link there between through a wireless protocol with a defined bonding procedure. The method also includes transmitting a static identification and dynamic seed from the PG device through a dedicated advertisement channel to the external device and generating a passkey from a pre-defined algorithm based on the dynamic seed and a static identification. Further, the method includes starting the defined bonding procedure.

In an embodiment, a system for initiating a secured bi-directional communication session with an implantable medical device. The system includes a pulse generator (PG) device and an external device configured to establish a communication link there between over a wireless protocol with a defined bonding procedure. The bonding procedure is initiated once the PG device and the external device generate a first and second passkey, respectively. The PG device includes one or more processors configured to transmit a static identification and a dynamic seed from the PG device through a dedicated advertisement channel to the external device. The one or more processors of the PG device are further configured to generate a first passkey at the PG device from a pre-defined algorithm based on the dynamic seed and a static identification. The external device includes one or more processors configured to generate a second passkey at the external device from the pre-defined algorithm based on the dynamic seed and the static identification.

BRIEF DESCRIPTION OF THE DRAWINGS

FIG. 1 illustrates simplified block diagram of an implantable medical device and an external device, according to an embodiment of the present disclosure.

DETAILED DESCRIPTION

The description that follows sets forth one or more illustrative embodiments. Embodiments described herein include imbedded medical devices (IMD) and external devices, and methods for establishing a secured communication link there between. It will be apparent that the teachings herein may be embodied in a wide variety of forms, some of which may appear to be quite different from those of the disclosed embodiments. While multiple embodiments are described, still other embodiments of the described subject matter will become apparent to those skilled in the art from the following detailed description and drawings, which show and describe illustrative embodiments of disclosed inventive subject matter. As will be realized, the inventive subject matter is capable of modifications in various aspects, all without departing from the spirit and scope of the described subject matter. Accordingly, the drawings and detailed description are to be regarded as illustrative in nature and not restrictive.

FIG. 1 illustrates a simplified block diagram of an implantable medical device (IMD) 101 and an external device 201 (e.g., table computer, smart phone, laptop, or the like) according to an embodiment. The IMD 101 may be implanted within a patient (e.g., proximate to the spinal cord). Additionally or alternatively, the IMD 101 may have components that are external to the patient, for example, the IMD 101 may include a neuro external pulse generator (EPG). The external device 201 is configured to establish a bi-directional communication link 140 with the IMD 101. The communication link 140 allows the external device 201 to receive measurements from the IMD 101, and to program or send instructions to the IMD 101. The bi-directional communication link 140 may use any standard wireless protocol such as Bluetooth Low Energy, Bluetooth, Wireless USB, Medical Implant Communication Service, WiFi, and the like. The external device 201 may be located within a home of the patient, a hospital, an automobile, at an office of the patient, or the like. The IMD 101 may be one of various types of implantable devices, such as, for example, neurostimulator, electrophysiology ("EP") mapping and radio frequency ("RF") ablation system, an implantable pacemaker, implantable cardioverter-defibrillator ("ICD"), defibrillator, cardiac rhythm management ("CRM") device, or the like.

Figure 2:
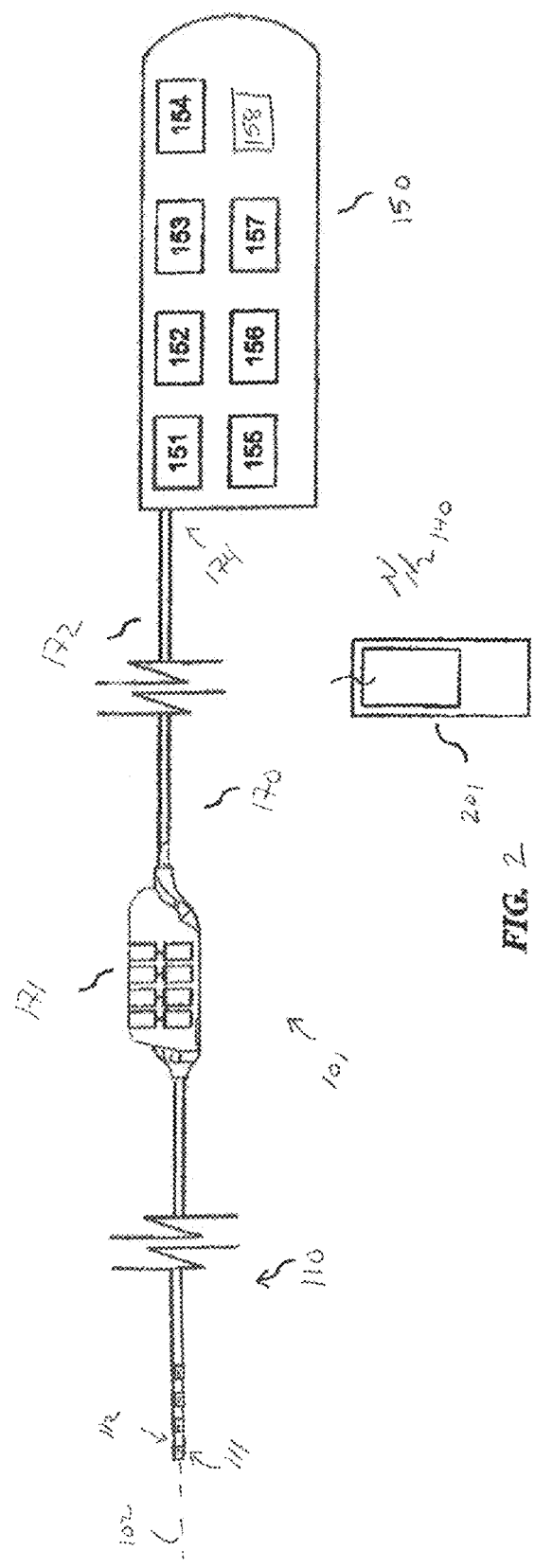
FIG. 2 illustrates a block diagram of exemplary internal components of the implantable medical device of FIG. 1, according to an embodiment of the present disclosure.

FIG. 2 depicts a block diagram of internal components of the IMD 101. For example, the IMD 101 may be a neurostimulator adapted to stimulate spinal cord tissue, peripheral nerve tissue, deep brain tissue, cortical tissue, cardiac tissue, digestive tissue, pelvic floor tissue, or any other suitable nerve tissue of interest within a patient's body.

The IMD 101 may include an implantable pulse generator (IPG) 150 that is adapted to generate electrical pulses applied to the tissue of a patient. Additionally or alternatively, the IPG 150 may be an external neuro pulse generator. The IPG 150 typically comprises a metallic housing that encloses a controller 151, pulse generating circuitry 152, a charging coil 153, a battery 154, RF circuitry 155, battery charging circuitry 156, switching circuitry 157, memory 158, and the like.

The controller 151 (also referred to herein as a processor module or unit) typically includes a microprocessor, or equivalent control circuitry, designed specifically for controlling the components of the IPG 150 and may further include RAM or ROM memory, logic and timing circuitry, state machine circuitry, and I/O circuitry. Typically, the controller 151 includes the ability to process or monitor input signals (data) as controlled by program code stored in memory. The details of the design and operation of the controller 151 are not critical to the invention. Rather, any suitable controller 151 may be used that carries out the functions described herein.

The IPG 150 may comprise a separate or an attached extension component 170. If the extension component 170 is a separate component, the extension component 170 may connect with a "header" portion 174 of the IPG 150 as is known in the art. If the extension component 170 is integrated with the IPG 150, internal electrical connections may be made through respective conductive components. Within the IPG 150, electrical pulses are generated by the pulse generating circuitry 152 and are provided to the switching circuitry 157. The switching circuitry 157 connects to outputs of the IPG 150. Electrical connectors (e.g., "Bal-Seal" connectors) within the connector portion 171 of the extension component 170 or within the IPG header may be employed to conduct various stimulation pulses. The terminals of one or more leads 110 are inserted within connector portion 171 or within the IPG header 174 for electrical connection with respective connectors. Thereby, the pulses originating from the IPG 150 are provided to the leads 110. The pulses are then conducted through the conductors of the lead 110 and applied to tissue of a patient via stimulation electrodes 111 that may be coupled to blocking capacitors. Any suitable known or later developed design may be employed for connector portion 171.

The stimulation electrodes 111 may be positioned along a horizontal axis 102 of the lead 110, and are angularly positioned about the horizontal axis 102 so the stimulation electrodes 111 do not overlap. The stimulation electrodes 111 may be in the shape of a ring such that each stimulation electrode 111 continuously covers the circumference of the exterior surface of the lead 110. Each of the stimulation electrodes 111 are separated by non-conducting rings 112, which electrically isolate each stimulation electrode 111 from an adjacent stimulation electrode 111. The non-conducting rings 112 may include one or more insulative materials and/or biocompatible materials to allow the lead 110 to be implantable within the patient. Non-limiting examples of such materials include polyimide, polyetheretherketone (PEEK), polyethylene terephthalate (PET) film (also known as polyester or Mylar), polytetrafluoroethylene (PTFE) (e.g., Teflon), or parylene coating, polyether bloc amides, polyurethane. The stimulation electrodes 111 may be configured to emit the pulses in an outward radial direction proximate to or within a stimulation target. Additionally or alternatively, the stimulation electrodes 111 may be in the shape of a split or non-continuous ring such that the pulse may be directed in an outward radial direction adjacent to the stimulation electrodes 111. Examples of a fabrication process of the stimulation electrodes 111 is disclosed in U.S. patent application Ser. No. 12/895,096, entitled, "METHOD OF FABRICATING STIMULATION LEAD FOR APPLYING ELECTRICAL STIMULATION TO TISSUE OF A PATIENT," which is expressly incorporated herein by reference.

It should be noted the stimulation electrodes 111 may be in various other formations, for example, in a planar formation on a paddle structure as disclosed in U.S. Provisional Application No. 61/791,288, entitled, "PADDLE LEADS FOR NEUROSTIMULATION AND METHOD OF DELIVERYING THE SAME," which is expressly incorporated herein by reference.

The lead 110 may comprise a lead body 172 of insulative material about a plurality of conductors within the material that extend from a proximal end of lead 110, proximate to the IPG 150, to its distal end. The conductors electrically couple a plurality of the stimulation electrodes 111 to a plurality of terminals (not shown) of the lead 110. The terminals are adapted to receive electrical pulses and the stimulation electrodes 111 are adapted to apply the pulses to the stimulation target of the patient. Also, sensing of physiological signals may occur through the stimulation electrodes 111, the conductors, and the terminals. It should be noted that although the lead 110 is depicted with four stimulation electrodes 111, the lead 110 may include any suitable number of stimulation electrodes 111 (e.g., less than four, more than four) as well as terminals, and internal conductors. Additionally or alternatively, various sensors (e.g., a position detector, a radiopaque fiducial) may be located near the distal end of the lead 110 and electrically coupled to terminals through conductors within the lead body 172.

For implementation of the components within the IPG 150, a processor and associated charge control circuitry for an IPG is described in U.S. Pat. No. 7,571,007, entitled "SYSTEMS AND METHODS FOR USE IN PULSE GENERATION," which is expressly incorporated herein by reference. Circuitry for recharging a rechargeable battery (e.g., battery charging circuitry 156) of an IPG using inductive coupling and external charging circuits are described in U.S. Pat. No. 7,212,110, entitled "IMPLANTABLE DEVICE AND SYSTEM FOR WIRELESS COMMUNICATION," which is expressly incorporated herein by reference.

An example and discussion of "constant current" pulse generating circuitry (e.g., pulse generating circuitry 152) is provided in U.S. Patent Publication No. 2006/0170486 entitled "PULSE GENERATOR HAVING AN EFFICIENT FRACTIONAL VOLTAGE CONVERTER AND METHOD OF USE," which is expressly incorporated herein by reference. One or multiple sets of such circuitry may be provided within the IPG 150. Different pulses on different stimulation electrodes 111 may be generated using a single set of the pulse generating circuitry 152 using consecutively generated pulses according to a "multi-stimset program" as is known in the art. Complex pulse parameters may be employed such as those described in U.S. Pat. No. 7,228,179, entitled "Method and apparatus for providing complex tissue stimulation patterns," and International Patent Publication Number WO 2001/093953 A1, entitled "NEUROMODULATION THERAPY SYSTEM," which are expressly incorporated herein by reference. Alliteratively, multiple sets of such circuitry may be employed to provide pulse patterns (e.g., tonic stimulation waveform, burst stimulation waveform) that include generated and delivered stimulation pulses through various stimulation electrodes of one or more leads 111 as is also known in the art. Various sets of parameters may define the pulse characteristics and pulse timing for the pulses applied to the various stimulation electrodes 111 as is known in the art. Although constant current pulse generating circuitry is contemplated for some embodiments, any other suitable type of pulse generating circuitry may be employed such as constant voltage pulse generating circuitry.

The stimulation parameters (e.g., amplitude, frequency, type of stimulation waveform) and other operating parameters of the IMD 101 may be non-invasively programmed into the memory 158 through the RF circuitry 155 in bi-directional wireless communication with the external device 201. For example, the external device 201 may permit the user to move electrical stimulation along and/or across one or more of the lead(s) 110 using different stimulation electrode 111 combinations, for example, as described in U.S. Patent Application Publication No. 2009/0326608, entitled "METHOD OF ELECTRICALLY STIMULATING TISSUE OF A PATIENT BY SHIFTING A LOCUS OF STIMULATION AND SYSTEM EMPLOYING THE SAME," which is expressly incorporated herein by reference. The controller 151 controls the RF circuitry 155 and receives data/transmissions from the RF circuitry 155. The RF circuitry 155 further allows status information relating to the operation of IMD 101 (as contained in the controller 151 or memory 158) to be sent to the external device 201 through an established bi-directional communication link 140.

The controller 151 may support a particular wireless communication protocol while communicating with the external device 201, such as Bluetooth low energy, Bluetooth, WiFi, Medical Implant Communication Service ("MICS"), or the like. Protocol firmware may be stored in memory 158, which is accessed by the controller 151. The protocol firmware provides the wireless protocol syntax for the controller 151 to assemble data packets, establish communication links 140, and partition data received from the external device 201.

The memory 158 may also contain a pre-defined algorithm that generates a passkey. The passkey may be used to initiate a bonding procedure between the IMD 101 and the external device 201 to establish a secured bi-directional communication session over the communication link 140. The passkey may be generated based on a dynamic seed and/or a static identification received by the RF circuitry 155 through the communication link 140 from the external device 201 and inputted into the pre-defined algorithm. Optionally, the dynamic seed may be a random number generated by the controller 151, based on the local system clock of the IMD 101, or the like that is transmitted by the RF circuitry 155 to the external device. Additionally or alternatively, the static identification may be stored on the memory 158 representing a product serial identification number of the IMD 101, which is a unique number assigned to the IMD 101 by a manufacturer of the IMD 101. Optionally, the static identification may be a pre-determined number stored on the memory 158 set by a clinician.

To establish the communication link 140 between the external device 201 and the IMD 101, the controller 151 instructs the RF circuitry 155 to transmit an advertisement notice on an advertisement channel. The advertisement channel is a point to multipoint, unidirectional, channel to carry a repeating pattern of system information messages such as network identification, allowable RF channels to establish the communication link 140, and the like that is included within the advertisement notice. The advertisement notice may be repeatedly transmitted after a set duration or an advertisement period until the IMD 101 receives a connection request from the external device 201 to form a communication link 140 and transmit within a data channel of the wireless protocol.

The length of the advertisement period may be adjusted by the controller 151 when entering an advertisement mode. During the advertisement mode, the controller 151 may reduce the length of the advertisement period relative to not being in the advertisement mode. The reduced length of the advertisement period results in the RF circuitry 155 transmitting more or an increased number of advertisement notices relative to not being in the advertisement mode. The controller 151 may enter the advertisement mode after detecting a predetermined signal directed at the IMD 101.

Figure 3:
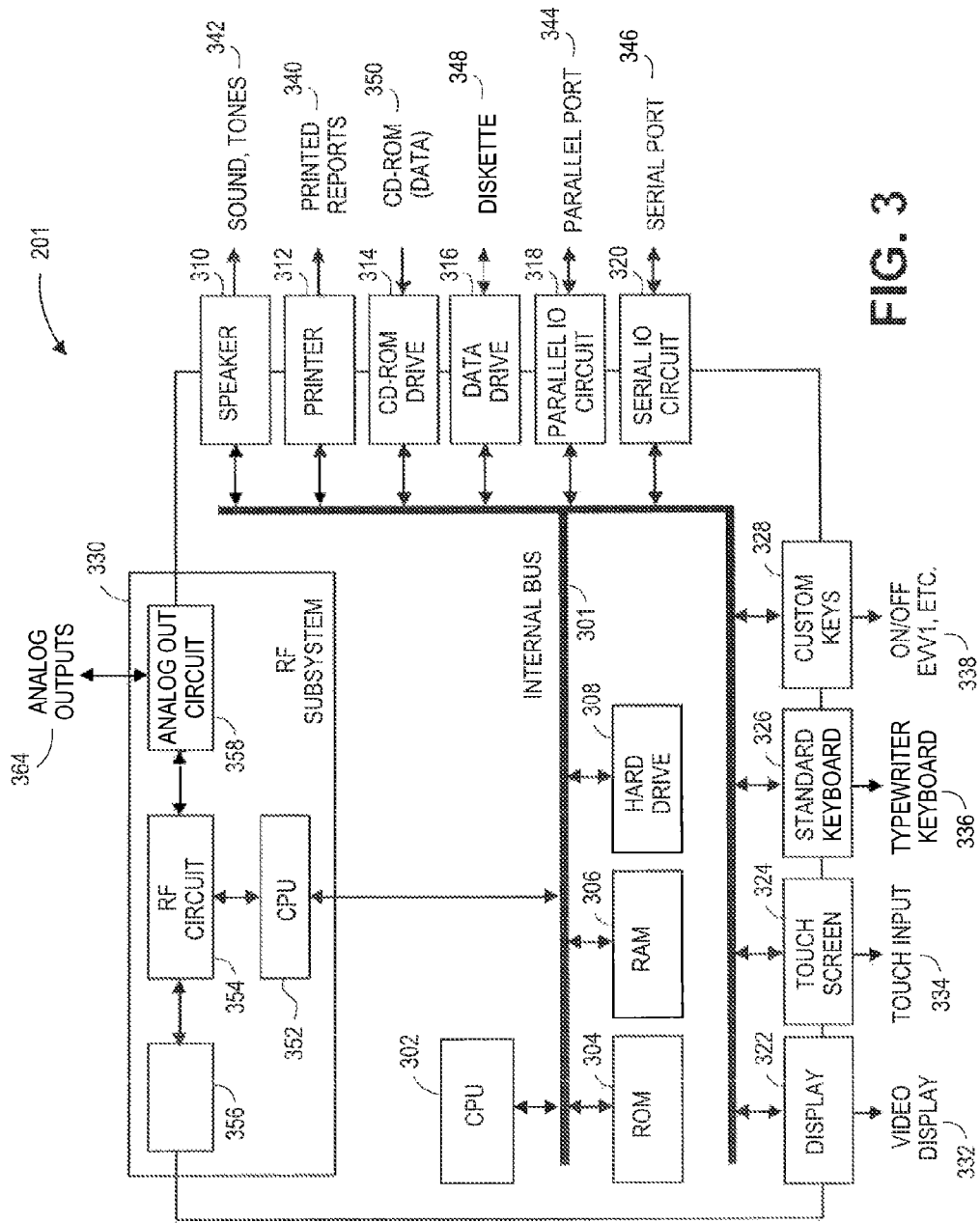
FIG. 3 illustrates a block diagram of exemplary internal components of the external device of FIG. 1, according to an embodiment of the present disclosure.

FIG. 3 illustrates a functional block diagram of the external device 201 that is operated in accordance with the processes described herein and to interface with the IMD 101 as described herein. The external device 201 may be a workstation, a portable computer, a tablet computer, an IMD programmer, a PDA, a cell phone and the like. The external device 201 includes an internal bus 301 that may connect/interface with a Central Processing Unit ("CPU") 302, ROM 304, RAM 306, a hard drive 308, a speaker 310, a printer 312, a CD-ROM drive 314, a floppy drive 316, a parallel I/O circuit 318, a serial I/O circuit 320, the display 322, a touchscreen 324, a standard keyboard 326, custom keys 328, and an RF subsystem 330. The internal bus 301 is an address/data bus that transfers information between the various components described herein. The hard drive 308 may store operational programs as well as data, such as stimulation waveform templates and detection thresholds.

The CPU 302 typically includes a microprocessor, a micro-controller, or equivalent control circuitry, designed specifically to control interfacing with the external device 201 and with the IMD 101. The CPU 302 may include RAM or ROM memory, logic and timing circuitry, state machine circuitry, and I/O circuitry to interface with the IMD 101. The display 322 (e.g., may be connected to the video display 332). The display 322 displays various information related to the processes described herein. The touchscreen 324 may display graphic information relating to the IMD 101 and include a graphical user interface. The graphical user interface may include graphical icons, scroll bars, buttons, and the like which may receive or detect user or touch inputs 334 for the external device 201 when selections are made by the user. Optionally the touchscreen 324 may be integrated with the display 322. The keyboard 326 (e.g., a typewriter keyboard 336) allows the user to enter data to the displayed fields, as well as interface with the RF subsystem 330. Furthermore, custom keys 328 turn on/off 338 (e.g., EVVI) the external device 201. The printer 312 prints copies of reports 340 for a physician to review or to be placed in a patient file, and the speaker 310 provides an audible warning (e.g., sounds and tones 342) to the user. The parallel I/O circuit 318 interfaces with a parallel port 344. The serial I/O circuit 320 interfaces with a serial port 346. The floppy drive 316 accepts diskettes 348. Optionally, the serial I/O port may be coupled to a USB port or other interface capable of communicating with a USB device such as a memory stick. The CD-ROM drive 314 accepts CD ROMs 350.

The RF subsystem 330 includes a central processing unit (CPU) 352 in electrical communication with an RF circuit 354, which may communicate with both memory 356 and an analog out circuit 358. The analog out circuit 358 includes communication circuits to communicate with analog outputs 364. The external device 201 may wirelessly communicate with the IMD 101 and utilize protocols, such as Bluetooth, Bluetooth low energy, WiFi, MICS, and the like. Alternatively, a hard-wired connection may be used to connect the external device 201 to the IMD 101.

Figure 4:
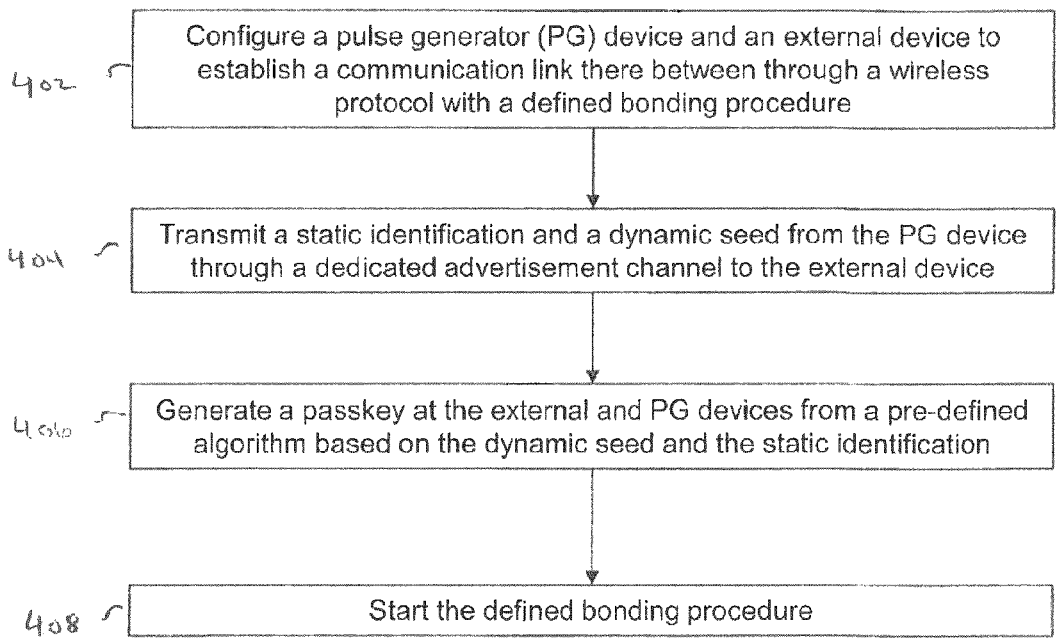
FIG. 4 illustrates a flowchart of a method for initiating a secured bi-directional communication session with an IMD.

FIG. 4 illustrates a flowchart of a method 400 for initiating a secured bi-directional communication session with an IMD (e.g., 101). The method 400 may be implemented as a software algorithm, package, or system that directs one or more hardware circuits or circuitry to perform the actions described herein. For example, the operations of the method 400 may represent actions to be performed by one or more circuits that include or are connected with processors, microprocessors, controllers, microcontrollers, Application Specific Integrated Circuits (ASICs), Field-Programmable Gate Arrays (FPGAs), or other logic-based devices that operate using instructions stored on a tangible and non-transitory computer readable medium (e.g., a computer hard drive, ROM, RAM, EEPROM, flash drive, or the like), such as software, and/or that operate based on instructions that are hardwired into the logic of the.

At least one technical effect of at least one portion of the methods described herein includes establishing a communication session with an IMD (e.g., 101) and an external device (e.g., 201) by i) configuring a pulse generator (PG) device and an external device to establish a communication link there between through a wireless protocol with a defined bonding procedure, ii) transmitting a static identification and a dynamic seed from the PG device through a dedicated advertisement channel to the external device, iii) generate a passkey at the external and PG devices from a pre-defined algorithm based on the dynamic seed and a static identification, iv) generate first and second pairing confirmation values at the external and PG devices based on at least the passkey generated by external and PG devices, and v) transmit the first and second pairing confirmation values to begin the defined bonding procedure.

Beginning at 402, the method configures a PG device (e.g., the IMD 101) and the external device 201 to establish the communication link 140 there between through a wireless protocol (e.g., Bluetooth low energy, Bluetooth) with a defined bonding procedure. The RF circuit 155 of the IMD 101 and the RF circuit 354 of the external device 201 may be configured to communicate utilizing Bluetooth Low Energy (or Bluetooth Smart), Bluetooth, MICS, WiFi, or the like. Examples of forming a communication link between an IMD and an external device is disclosed in U.S. patent application Ser. No. 14/091,809, entitled, "SYSTEM AND METHODS FOR ESTABLISHING A COMMUNICATION SESSION BETWEEN AN IMPLANTABLE MEDICAL DEVICE AND AN EXTERNAL DEVICE," which is expressly incorporated herein by reference.

Figure 5:
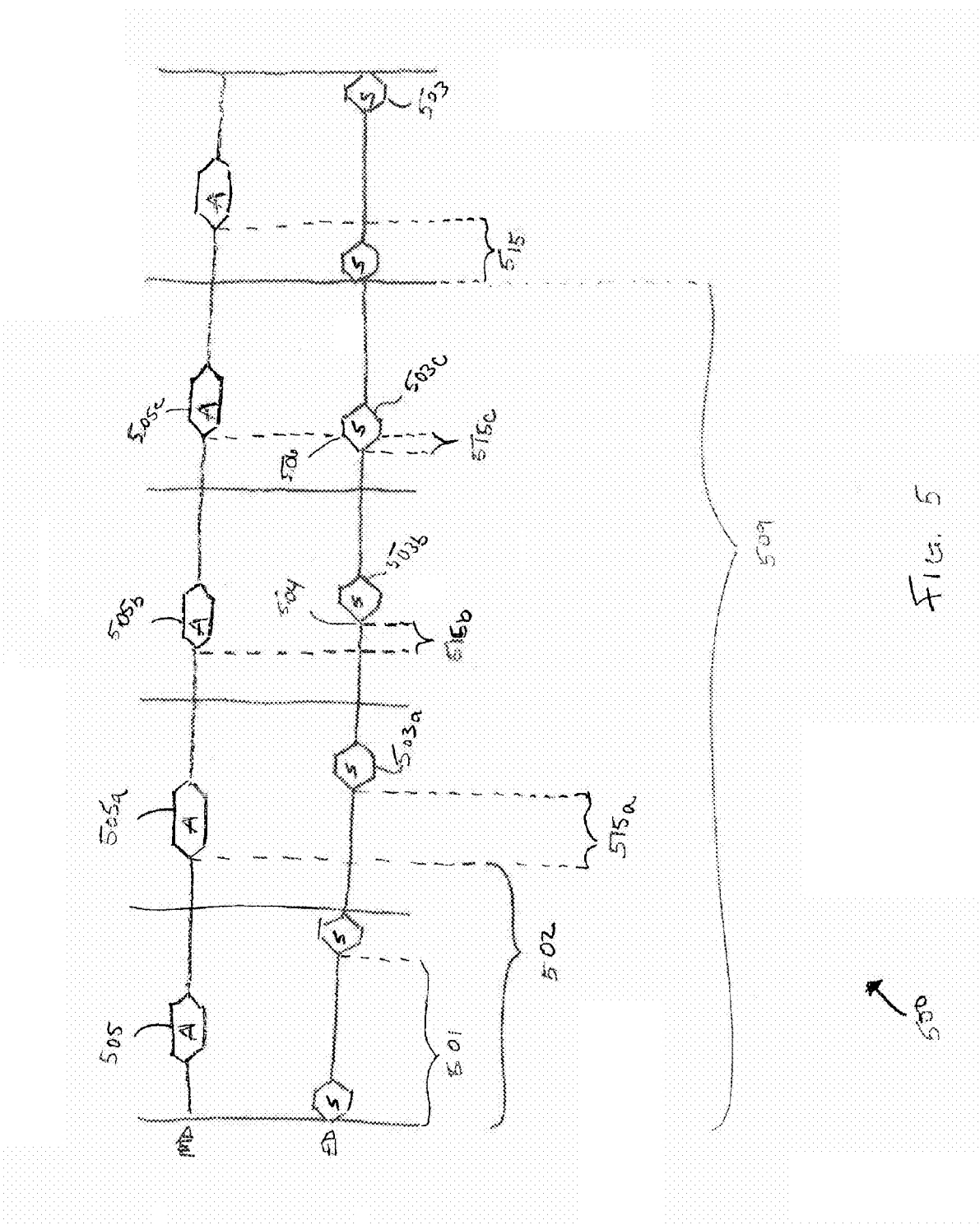
FIG. 5 illustrates a timing diagram between an IMD and an external device to establish a communication link, according to an embodiment of the present disclosure.

For example, FIG. 5 illustrates a timing diagram 500 between the IMD 101 and the external device 201 to establish the communication link 140, according to an embodiment of the present disclosure. The IMD 101 and the external device 201 use a wireless protocol (e.g., Bluetooth low energy) that utilizes a specified frequency for an advertisement channel. The IMD 101 transmits an advertisement notice 505 on the advertisement channel using the RF circuitry 155. The advertisement notice may contain frequency synchronization information utilized to form the communication link 140, address information of the IMD 101, address information of the external device 201, the static identification of the IMD 101, the dynamic seed, and the like. The advertisement notice 505 may be repeated, at a set or variable interval or advertisement period 502, until the communication link 140 is established. The advertisement period 502 represents the length of time the IMD 101 may transmit another advertisement notice 505 after a previous transmission by the IMD 101 of the advertisement notice 505. Optionally, the advertisement period 502 may be input by a user (e.g., physician using an external device).

The advertisement period 502, for example, may be 5 seconds such that the advertisement notice 505 may be repeated every 5 seconds. Optionally, the advertisement period 502 may be longer or shorter than the above example. Additionally or alliteratively, the advertisement period may be predetermined and stored in memory 158 of the IMD 101.

The user, using the touchscreen 324 or standard keyboard 336, may instruct the external device 201 to establish the communication link 140 with the IMD 101. The CPU 302 instructs the RF subsystem 330 to output the received transmissions from the advertisement channel (e.g., 2402 MHz, 2426 MHz, 2480 MHz), for example, every 1 s. The output of the RF subsystem 330 corresponds to a scanning interval 503. The RF subsystem repeats the scanning interval 503 every scan period 501 such that the scanning interval 503 may be repeated, for example, every 4 s. The scanning interval 503 and/or scan period 501 may be longer or shorter than the above example. Additionally or alternatively, the scanning interval 503 and/or scan period 501 may be a predetermined length stored on the ROM 304, the RAM 306, or the hard drive 308. Optionally, the scanning interval 503 and/or scan period 501 is configured by the user, such that, the scanning interval 503 or period 501 may be increased or decreased. The RF subsystem 330 continually repeats the scanning interval 503 until the CPU 302 acknowledges receipt of the advertisement notice 505.

The scan period 501 and the advertisement period 502 occur independent and asynchronous with respect to one another, such that the advertisement notices 505 intermittently overlap the scan intervals at 504 and 506. Each period length is predetermined from distinct and separate sources. The scan period 501 is predetermined or configured by the user of the external device 201. Separately, the advertisement period 502 is predetermined by the protocol syntax stored in the memory 158 of the IMD 101. One of the scan period 501 and the advertisement period 502 may be altered, while, the length of the other period (e.g., advertisement period 502, scan period 501) remains constant.

The scan period 501 has an asynchronous phased relation with respect to the advertisement period 502 in order that a phase interval 515 between beginnings of the scanning intervals 503 and advertisement notices 505 continuously (or intermittently) changes. For example, the scan period 501 may be 4 s having the scanning interval 503 of 1 s, and advertisement period 502 may be 5 s having the advertisement notice 505 of 1.5 s. The different lengths of the periods 501 and 502 represent the asynchronous phased relationship with respect to each other. The asynchronous phased relationship causes the advertisement notice 505 and the scanning interval 503 to begin at different times thus creating phase intervals 515. The length of the phase interval 515 can be extended or shortened by changing the advertisement period 502 of the IMD 101 or the scan period 501 of the external device 201. Thus, by configuring the advertisement period 502 or the scan period 501, the phase interval 515 may continuously change or be changed intermittently after a set number of cycles. The beginning of the cycle occurs at the transmission of the advertisement notice 505 or the scan interval 503. The phase interval 515 may be controlled by the user changing the scan period 503 of the external device 201 or by the controller 151 changing the advertisement period 502 of the IMD 101.

For example, the phase interval 515 of the timing diagram 500, is continuously changing after each cycle. The phase interval 515a, measured between the beginning of the advertisement notice 505a and the beginning of the scan interval 503a, may be approximately 1.5 s. The advertisement notice 505a and the scanning interval 503a do not partially or wholly overlap. The phase interval 515b, between the advertisement notice 505b and the scanning interval 503b, may be approximately 750 ms. The phase interval 515c, between the advertisement notice 505c and the scanning interval 503c, may be approximately 250 ms. Accordingly, the length of the phase interval 515 continuously changes each cycle. The changes in the length of the phase interval 515 cooperate such that each cycle or repetition of the scanning interval 503 and the advertisement notice 505 shifts with respect to each other, thereby allowing for partially overlapping events at 504 and 506 to occur. For instance, only the phase intervals 515b-515c are associated with partially overlapping advertisement notices 505b-c and scanning intervals 515b-c. Although the periods 501, 502 are asynchronous, the scanning intervals 502 and the advertisement notices 505 will partially overlap and enable the external device 201 intermittently or after a set number of cycles to receive the advertisement notice 505. The overlaps occur intermittently, in that after a number of cycles the scanning interval 503 and advertisement notice 502 will partially overlap in fewer cycles than the number of cycles. For example, the scanning interval 503 and advertisement notice 502 partially overlap after the fourth and fifth cycle of the scanning interval 503 or the third and fourth cycle of the advertisement notice 505.

Optionally, the IMD 101 may have an advertisement mode that decreases the number of cycles needed until the communication link 140 is established, by increasing the likelihood of the scanning interval 503 partially overlapping the advertisement notice 505. During an advertisement mode, the controller 151 may decrease the length of the advertisement period 502, relative to not being in the advertisement mode, thus, increasing the number of advertisement notices 505 in a time frame 509. The increased number of advertisement notices 505 increase the number of partial overlaps with the scanning intervals 503, allowing the external device 201 to detect or receive the advertisement notice 505 in a shorter amount of cycles relative to the IMD 101 that is not in an advertisement mode.

Once the external device 201 receives the advertisement notice 505, in the form of a data packet transmitted from the IMD 101, the CPU 302 analyzes or compares the data packet with the protocol syntax stored on the ROM 304, the RAM 306, or the hard drive 308. The protocol syntax may include the structure of an advertisement notice (e.g., data packet specifications, appropriate number of bits, frequency, or the like) utilized by the wireless protocol. Optionally, the advertisement notice 505 may include a unique code designating the packet as an advertisement. By comparing the protocol syntax with the data packet, the CPU 302 determines whether the received data packet is an advertisement notice 505 using the wireless protocol of the external device 201. If the received data packet is determined not to be an advertisement notice, the external device 201 may continue scanning the advertisement channel. When the CPU 302 determines that the data packet received by the RF circuit 354 is the advertisement notice 505 (having the proper syntax), the CPU 302 outputs a connection request (e.g., data packet) to be transmitted by the RF circuit 354 along the advertisement channel.

The CPU 302 constructs a data packet representing the connection request by adding packet frames to conform to the protocol such as the address of the IMD 101 and/or external device 201, error detection codes such as CRC, a payload, or the like. The payload may include connection instructions (e.g., frequency of the data channel for the communication link 140) from the user intended for the IMD 101. Optionally, the data packet may include a static identification of the external device 201 and a dynamic seed. Once the data packet has been formed, the CPU 302 outputs the data packet to the RF subsystem 330 to be transmitted along the advertisement channel that was to the IMD 101.

The RF circuit 155 receives the data packet and outputs to the controller 151. The controller 151 may store the data packet in memory 158 for analysis. The controller 151 determines whether the data packet is in response to the advertisement notice 505 by comparing the address information of the data packet with the address transmitted by the IMD 101 within the advertisement notice 505. If the address information matches, the controller 151 partitions the payload from the data packet and carries out the instruction of the connection request from the payload by comparing the instructions to a stored Instruction set on the memory 158 for the wireless protocol. Optionally, the controller 151 may compare the address information of the external device 201 on the data packet with a permissible links table stored in memory 158 to determine whether the IMD 101 should ignore or partition the payload of the data packet. Once the controller 151 identifies the connection request, controller 151 may instruct the RF circuit 155 to monitor the data channel identified in the connection request for further instructions from the external device 201, establishing the communication link 140.

Figure 6:
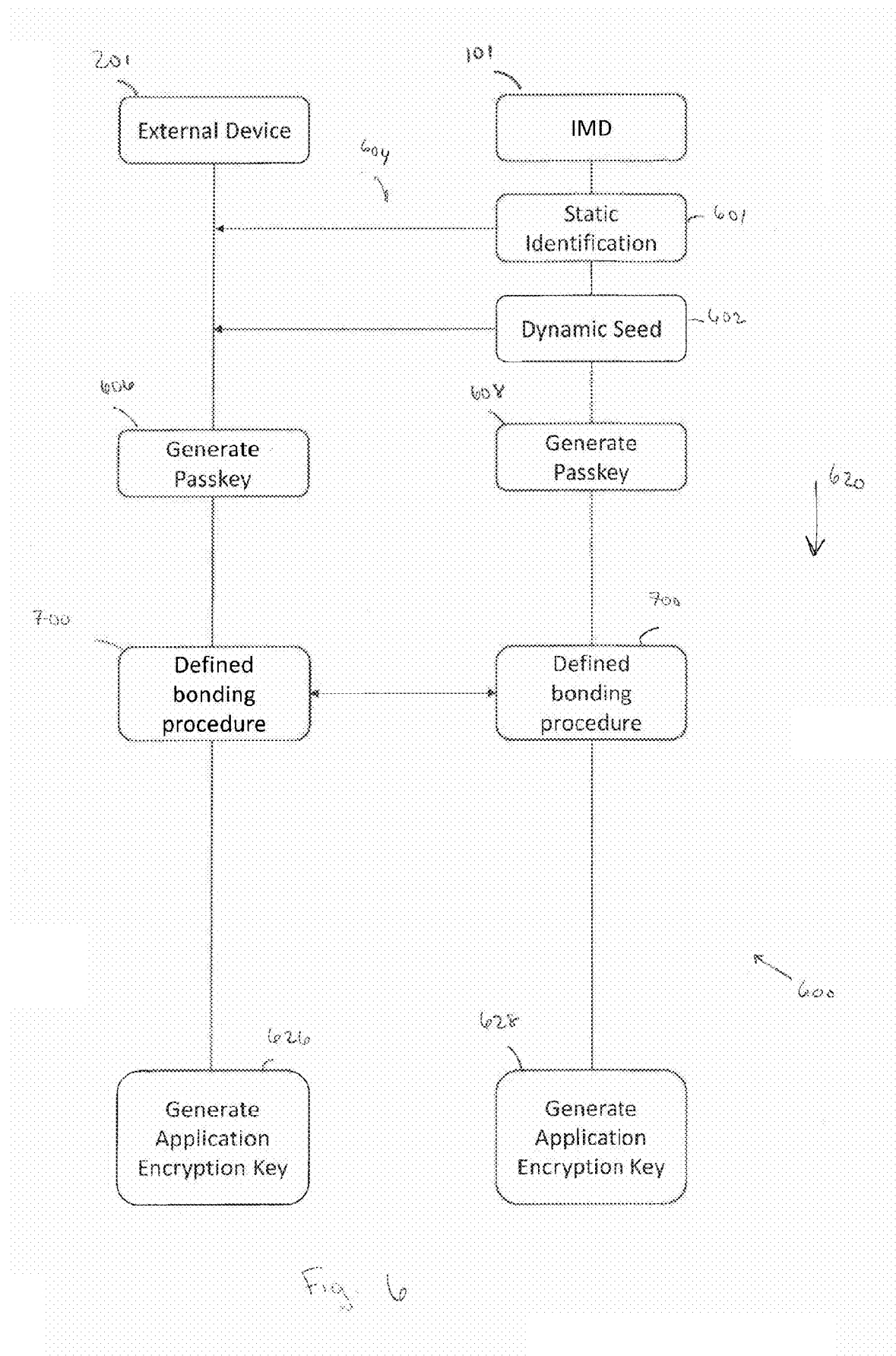
FIG. 6 illustrates a message sequence chart between an IMD and an external device, according to an embodiment of the present disclosure.

Returning to FIG. 4, the method 400 transmits (at 404) the dynamic seed and the static identification seed from the PG device (e.g., the IMD 101) through a dedicated advertisement channel to the external device 201. FIG. 6 illustrates a message sequence chart 600 between the external device 201 and the IMD 101. The message sequence chart 600 illustrates the communications between the external device 201 and the IMD 101 over the advertisement and data channel through the communication link 140 defined by the wireless protocol. A vertical arrow 620 represents the progression of time. A dynamic seed 602 may be generated by, for example, the controller 151, of the IMD 101 through a random number generator and stored on memory (e.g., the memory 158). Optionally, the dynamic seed 602 may be generated from the local system clock of the IMD 101.

Once the dynamic seed 602 is generated, the controller 151 may generate an encrypted static identification 601 from an encryption algorithm based on the dynamic seed 602 and the static identification. The encryption algorithm may be stored on the memory 158. The controller 151 may include the encrypted static identification 601 and the dynamic seed 602 within a payload of a data packet 604 transmitted by the RF circuitry 155 along the advertisement channel. The dynamic seed 602 and the encrypted static identification 601 may be received by the external device 201 through the RF circuit 354 and partitioned from the data packet 604 by the CPU 302 and/or 352 and stored on memory (e.g., ROM 304, RAM 306, memory 356, the hard drive 308).

Once the encrypted static identification 601 is partitioned from the data packet 604, the external device 201 may perform a decryption algorithm on the encrypted static identification 601 based on the dynamic seed 602. The decryption algorithm allows the external device 201 to determine the static identification of the IMD 101. Optionally, the external device 201 may transmit a confirmation packet that instructs the IMD 101 to generate a passkey to initiate a bonding procedure under the wireless protocol.

Additionally or alternatively, the IMD 101 may transmit the static identification without being encrypted, which may allow the dynamic seed 602 to be generated by the external device 201. For example, the IMD 101 transmits the static identification within the payload of a data packet along the advertisement channel. The external device 201 receives the data packet through the RF circuit 354 and partitions the static identification from the data packet 604 by the CPU 302 and/or 352 and stores the static identification on memory (e.g., ROM 304, RAM 306, memory 356, the hard drive 308). The CPU 302 and/or 352 may determine based on not receiving the dynamic seed from the IMD 101 to generate the dynamic seed using a random number generator, the system clock of the external device 201, and the like at the external device 201. Once the dynamic seed is generated, the dynamic seed may be included within a payload of a data packet transmitted by the RF circuit 354 along the data channel. The dynamic seed may be received by the IMD 101 through the RF circuitry 155 and partitioned from the data packet by the controller 151 and stored on the memory 158. Optionally, the external device 201 may include the dynamic seed in a subsequent data packet, along the data channel, after the connection request to establish the communication link 140 (described above) over the advertisement channel is transmitted.

Returning to FIG. 4, the method 400 generates (at 406) a passkey at the external and PG devices 201 and 101 from a pre-defined algorithm based on the dynamic seed and the static identification. The pre-defined algorithm may be stored on the memory 158 of the IMD 101 and the memory (e.g., ROM 304, RAM 306, memory 356, the hard drive 308) of the external device 201. The CPU 302 or 352 may access the pre-defined algorithm and input the dynamic seed and the stored identification once the data packet 604 was transmitted. The pre-defined algorithm may generate the passkey 606 from the dynamic seed 602 and the static identification. Additionally, the controller 151 may access the pre-defined algorithm and input the dynamic seed and the stored identification to generate the passkey 608 once the data packet 604 was received by the RF circuitry 155. It should be noted that the same dynamic seed and the static identification is used for the external device 201 and the IMD 101 to generate the passkeys 606 and 608.

As described above, the static identification may originate from the IMD 101 and transmitted through the communication link 140 to the external device 201. The static identification, unlike the dynamic seed, may be the same value to generate multiple passkeys 606 and 608 at different sessions. It should be noted, that the encrypted static identification, generated based on the dynamic seed, may be different or unique compared to different sessions. The static identification may be a pre-determined number stored on the memory (the memory 158, the memory 356, ROM 304, RAM 306, the hard drive 308) unique for each device. The static identification is used by both of the devices 201 and 101 to generate the passkeys 606 and 608. Later, the communication link 140 is terminated by the user of the external device 201. During a separate session with the external device 201 and the IMD 101, the external device 201 may again receive the static identification, from the encrypted static identification within the advertisement packet payload, which will be used to generate the passkeys 606 and 608. Optionally, the static identification and/or dynamic seed may be transmitted from the IMD 101 to the external device 201 within a data packet after the communication link 140 is established.

Returning to FIG. 4, the method 400 starts (at 408) the defined bonding procedure. The bonding procedure establishes an encryption key 726 and 728 used by the external device 201 and the IMD 101. The encryption key 726 and 728 allows the external device 201 and the IMD 101 to encrypt and decrypt data packets transmitted over the communication link 140. The encrypted data packets prohibit devices without the encryption key 726 and 728 from interpreting the data packets. The encryption key 726 and 728 is based on the generated passkeys 606 and 608. If the passkeys 606 and 608 generated by the external device 201 and the IMD 101 do not match, the bonding procedure will fail and the communication link 140 will be terminated.

Figure 7:
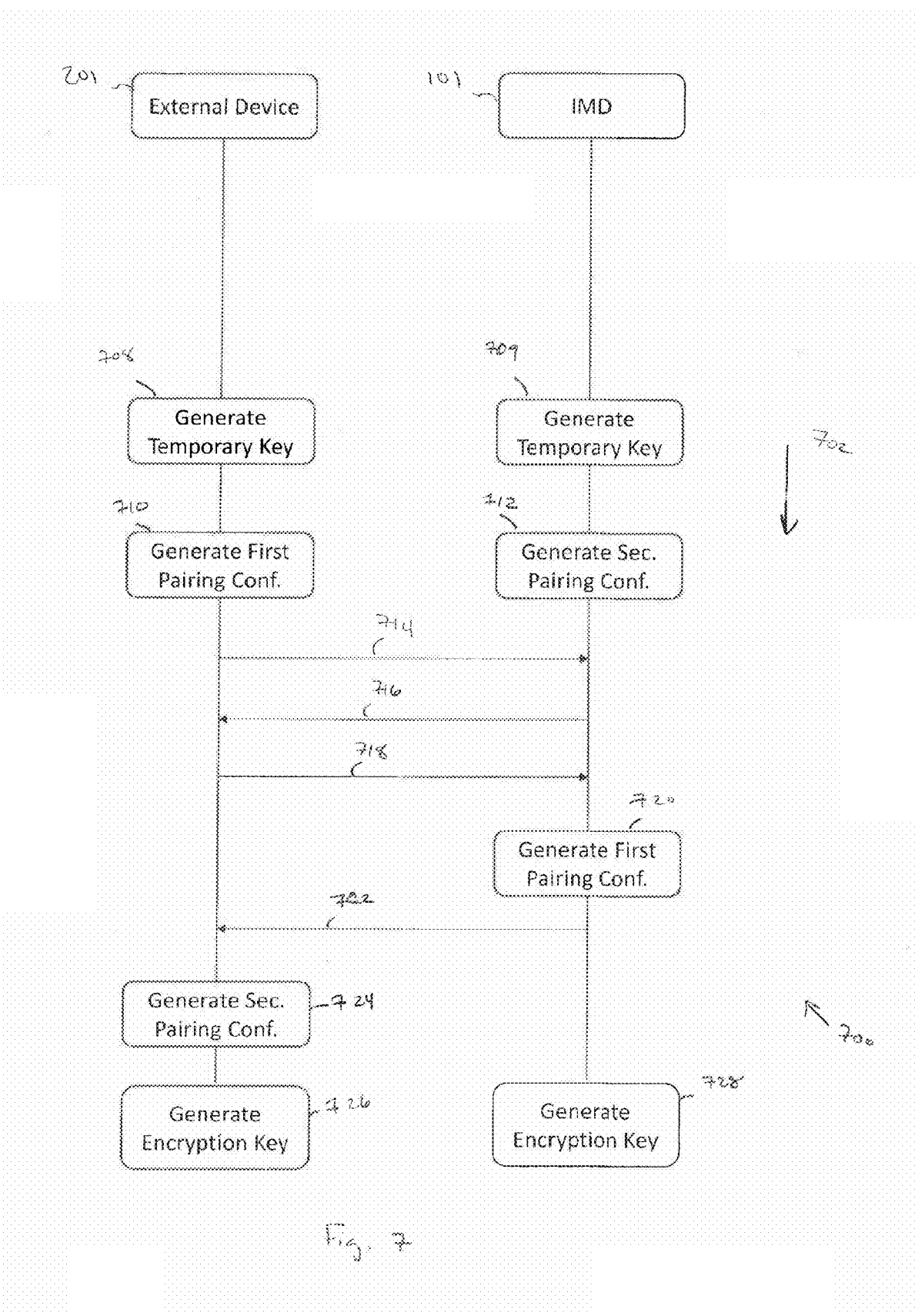
FIG. 7 illustrates a message sequence chart between an IMD and an external device during a defined bonding procedure, according to an embodiment of the present disclosure.

FIG. 7 illustrates a message sequence chart 700 between the external device 201 and the IMD 101 during a bonding procedure, in accordance with an embodiment. A vertical arrow 702 represents the progression of time. During the bonding procedure, the external device 201 and the IMD 101 generate temporary keys 708 and 709, which may be based on the generated passkeys 606 and 608 at the external device 201 and the IMD 101, the static identification, the dynamic seed 602. Once the temporary keys 708 and 709 are generated the external device 201 and the IMD 101 may generate first and second pairing confirmation values 710 and 712. The first and second pairing confirmation values 710 and 712 may be a predetermined acknowledgement codes defined by the wireless protocol and stored on the memory (e.g., the memory 158, the memory 356, ROM 304, RAM 306, the hard drive 308) of each device 201 and 101. The first and second pairing confirmation values 710 and 712 are generated using the passkeys 606 and 608 generated by the devices 201 and 101, respectively. The first and second pairing confirmation values 710 and 712 may be transmitted by each device 201 and 101 within data packets 714 and 716, respectively. Once each of the first and second pairing confirmation values 710 and 712 are received, the devices 201 and 101 may partition and deconstruct the confirmation values 710 and 712 using the passkey 606 and 608 of the respective device 201 and 101. The deconstructed confirmation values may be compared with the predetermined acknowledgement codes on the memory of the devices 201 and 101. If the deconstructed confirmation values match the predetermined acknowledgement codes, the CPU 302 and the controller 151 may determine that the generated passkeys 606 and 608 of each device 201 and 101 match and the bonding procedure may continue (e.g., generate encryption keys 726 and 728). Alternatively, if the deconstructed confirmation values do not match, the communication link 140 may be terminated by the respective device 201 and 101. It should be noted that the passkeys 606 and 608 are not transmitted between either device 201 and 101, rather generated values based on the passkeys 606 and 608 are communicated.

Additionally or alternatively, the first and second pairing confirmation values 710 and 712 may be based on a first and second test value, respectively. For example, the external device 201 generates the first pairing confirmation value 710 based on the passkey 606 and the first test value. The first test value, for example, may be a random value determined by the CPU 302. The first pairing confirmation value 710 is transmitted to the IMD 101 within a payload of a data packet 714.

Likewise, the IMD 101 generates the second pairing confirmation value 712 based on the passkey 608 and the second test value. The second test value, for example, may be a random value determined by the controller 151. The second pairing confirmation value 712 is transmitted to the external device 201 within a payload of the data packet 716. Once the data packet 716 is received, the external device 201 may transmit a data packet 718 that includes the first test value used by the external device 201 to generate the first pairing confirmation value 710. The IMD 101 may attempt to re-generate the first pairing confirmation value 720 (also referred to as a third or new pairing confirmation value) using the passkey 608 and the first test value. The IMD 101 may compare the third pairing confirmation value with the first pairing confirmation value 710. If the first and third pairing confirmation values match, the controller 151 may determine that the external device 201 is using the appropriate passkey and may proceed with the bonding procedure. Alternatively, if the values do not match, the IMD 101 may terminate the communication link 140.

Once the controller 151 determines that the values match, the IMD 101 may transmit a data packet 722 that includes the second test value used to generate the second pairing confirmation value 712. The external device may attempt to re-generate the second pairing confirmation value 712 (also referred to as a fourth or new pairing confirmation value) using the passkey 606 and the second test value. If the second and fourth pairing confirmation values match, the CPU 302 may determine that the IMD 101 is using the appropriate passkey and may proceed with the bonding procedure. Alternatively, if the values do not match, the external device 201 may terminate the communication link 140.

In embodiments, optionally, the external device 201 and the IMD 101 utilize the Bluetooth Low Energy ("BLE") protocol. The BLE protocol is defined within "Bluetooth Specification Version 4.1, published Dec. 3, 2013 (incorporated herein by reference). For example, the BLE protocol includes a security manager that uses a key distribution approach to perform identity and encryption functionalities that is performed using a bonding procedure to establish an encryption key in two phases. In the first phase pairing request is transmitted by an initiator to a responder. In the second phase a short term key (STK) (e.g., encryption key) is generated. The encryption key (e.g., a short term key (STK)) is determined based on a predefined function defined within the BLE protocol that uses a 128-bit temporary key (TK) that is translated from a randomly generated six digit passkey.

For example, the pairing request may be included within the data packet 604 transmitted by the external device 201 with the dynamic seed 602. Optionally, the pairing request may be initiated by the external device 201 as a confirmation packet. Additionally or alternatively, the IMD 101 may transmit the pairing request within the data packet 604. The TK may be translated from the passkeys 606 and 608 generated by the external device 201 and the IMD 101, the static identification, and/or the dynamic seed 602, which may also be used to generate encryption keys 726 and 728.

Once the bonding procedure 700 is complete, the communication link 140 between the external device 201 and the IMD 101 is encrypted. Optionally, the external device 201 and the IMD 101 may generate an application encryption key 626 and 628 to be used by user software of the external device 201. For example, the clinician may be running a program or application on the external device 201. The program initiates a security procedure, which requires verification that the external device 201 and the IMD 101 are paired correctly before the external device 201 may program or adjust/access settings of the IMD 101. The application encryption key 626 and 628 may be generated by the external device 201 and the IMD 101 from an application encryption algorithm based on the passkey 606 and 606 generated at the respective devices, the static identification, the dynamic seed, or the like. Once the application encryption keys 626 and 628 are generated the application on the external device 201 may encrypt data or requests based on the application encryption key 626 and 626. If the IMD 101 and/or external device 201 did not generate a matching passkey, the external device 201 has an incorrect static identification and/or dynamic seed the communications between the devices would not be able to correctly determine the instructions from the external device 201 resulting in the communication link 140 being terminated by the application.

The controller 151 and CPUs 302 and 352 may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally or alternatively, the controller 151 and CPUs 302 and 352 represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The controller 151 and CPUs 302 and 352 may execute a set of instructions that are stored in one or more storage elements, in order to process data. The storage elements may also store data or other information as desired or needed. The storage element may be in the form of an information source or a physical memory element within the controller 151 and CPUs 302 and 352. The set of instructions may include various commands that instruct the controller 151 and CPUs 302 and 352 to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional Items.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. §112(f), unless and until such claim limitations expressly use the phrase "means for" followed by a statement of function void of further structure.

What is claimed is:

1. A method for initiating a secured bi-directional communication session with an implantable medical device, the method comprises:
   configuring a pulse generator (PG) device and an external device to establish a communication link there between through a wireless protocol with a defined bonding procedure;
   transmitting a static identification and a dynamic seed from the PG device through a dedicated advertisement channel to the external device;
   generating a passkey at the external and PG devices from a pre-defined algorithm based on the dynamic seed and a static identification; and
   once the passkey is generated by the external and PG devices, starting the defined bonding procedure.

2. The method of claim 1, wherein the bonding procedure includes generating first and second pairing confirmation values at the external and PG devices based on at least the passkey generated by the external and PG devices, respectively.

3. The method of claim 1, further comprising encrypting the static identification based on the dynamic seed at the PG prior to the transmitting operation.

4. The method of claim 1, further comprising transmitting, from the PG device, advertisement notices over a dedicated advertisement channel according to the wireless protocol, wherein the advertisement notices include the static identification and the dynamic seed; and
   when the external device detects one of the advertisement notices, establishing the communication link between the external and PG devices.

5. The method of claim 1, wherein the protocol constitutes a Bluetooth low energy protocol.

6. The method of claim 1, wherein the static identification is a model number of the second device.

7. The method of claim 1, wherein the PG device is an implantable medical device (IMD).

8. The method of claim 1, wherein the PG device enters an advertising mode, during which the transmitting operations are performed in accordance with a Bluetooth Discovery Service defined within the protocol.

9. The method of claim 1, further comprising once the bonding procedure is complete, generating an application key at the external and PG device based on the dynamic seed and a static identification.

10. A system for initiating a secured bi-directional communication session with an implantable medical device comprising:
    a pulse generator (PG) device and an external device configured to establish a communication link there between over a wireless protocol with a defined bonding procedure, wherein the defined bonding procedure is initiated once the PG device and the external device generate a first and second passkey, respectively;
    the PG device includes one or more processors configured to transmit a static identification and a dynamic seed from the PG device through a dedicated advertisement channel to the external device, and the one or more processors are further configured to generate a first passkey at the PG device from a pre-defined algorithm based on the dynamic seed and a static identification;
    the external device includes one or more processors configured to generate a second passkey at the external device from the pre-defined algorithm based on the dynamic seed and the static identification.

11. The system of claim 10, wherein the boding procedure includes each device generating a first and second pairing confirmation values at the external and PG devices based on at least the passkey generated by the external and PG devices, respectively based on the first and second passkeys.

12. The system of claim 10, wherein the first pairing confirmation value is based in part on a first test value; and
    wherein the second pairing confirmation value is based in part on a second test value.

13. The system of claim 12, wherein the one or more processors of the PG device are configured to encrypt the static identification based on the dynamic seed at the PG prior to the transmitting operation.

14. The system of claim 10, wherein the PG device is further configured to transmit advertisement notices over a dedicated advertisement channel according to the wireless protocol, wherein the advertisement notices include the static identification and the dynamic seed; and the external device is configured to establish the communication link when one of the advertisement notices is detected by the external device.

15. The system of claim 10, wherein the wireless protocol constitutes a Bluetooth low energy protocol.

16. The system of claim 10, wherein the static identification is a model number of the PG device or external device.

17. The system claim 10, wherein the PG device enters an advertising mode, during which the transmitting operations are performed in accordance with a Bluetooth Discovery Service defined within the wireless protocol.

18. The system of claim 10, wherein the PG device is an implantable medical device (IMD).

\* \* \* \* \*